US00PP29098P2

(12) United States Plant Patent
Eveleens

(10) Patent No.: US PP29,098 P2
(45) Date of Patent: Mar. 13, 2018

(54) ***HYDRANGEA* PLANT NAMED 'HORT 10-080-01'**

(50) Latin Name: *Hydrangea macrophylla*
Varietal Denomination: Hort 10-080-01

(71) Applicants: Horteve Breeding BV, De Kwakel (NL); Kolster Holding BV, Boskoop (NL)

(72) Inventor: Cornelis Pieter Eveleens, De Kwakel (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 15/330,660

(22) Filed: Oct. 24, 2016

(51) Int. Cl.
*A01H 5/00* (2006.01)

(52) U.S. Cl.
USPC ..... Plt./250

(58) Field of Classification Search
USPC ..... Plt./226, 250
See application file for complete search history.

(56) References Cited

PUBLICATIONS

UPOV-PLUTO: Plant Variety Database, Oct. 27, 2017, citation for 'Hort 10-080-01'. 1 page.*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Hydrangea macrophylla* plant named 'Hort 10-080-01' that is characterized by its upright, compact plant habit, its double flowers with a large number of sepals, its sterile flowers with sepals that are pink in the color with a white edge, and its sterile flowers that are star-shaped with sepals that are ovate in shape with pointed tips.

2 Drawing Sheets

Botanical classification: *Hydrangea macrophylla.*
Varietal denomination: 'Hort 10-080-01'.

CROSS REFERENCE TO RELATED APPLICATIONS

This application is related to a plant breeders' rights application filed in Europe on Oct. 28, 2014, application No. 2014/2684. There have been no offers for sale anywhere in the world more than one year prior to the filing of this application, any sales less than one year were under the direction of the Inventor and no accessibility to one of ordinary skill in the art could have been derived from the printed plant breeder's rights documents.

This application is co-pending with U.S. Plant Patent Applications filed for plants derived from the same breeding program that are entitled *Hydrangea* Plant Named 'Hort 10-087-01' (U.S. Plant patent application Ser. No. 15/330,657) and *Hydrangea* Plant Named 'HORT 10-087-07' (U.S. Plant patent application Ser. No. 15/330,659).

BACKGROUND OF THE INVENTION

The present invention relates to a new and distinct cultivar of *Hydrangea macrophylla* and will be referred to hereafter by its cultivar name, 'Hort 10-080-01'. 'Hort 10-080-01' represents a new bigleaf *hydrangea*, a perennial shrub grown for landscape use.

'Hort 10-080-01' was derived from an ongoing controlled breeding program directed by the Inventor. The objectives of the breeding program include developing new cultivars of

*Hydrangea* with double flowers combined with compact plant habits and floriferous blooming habits. 'Hort 10-080-01' arose from a controlled cross made by the Inventor in Boskoop, The Netherlands in June of 2009 between unnamed and unpatented proprietary plants in the Inventor's breeding program; reference no. 08-021-05 as the female parent and reference no. 08-021-04 as the male parent. 'Hort 10-080-01' was selected as a single unique plant from amongst the resulting seedlings in June of 2014.

Asexual propagation of the new cultivar was first accomplished by stem cuttings by the Inventor in Boskoop, The Netherlands in July of 2011. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hort 10-080-01' as a unique cultivar of *Hydrangea macrophylla.*

1. 'Hort 10-080-01' exhibits an upright, compact plant habit.
2. 'Hort 10-080-01' exhibits double sterile flowers with a large number of sepals.
3. 'Hort 10-080-01' exhibits sterile flowers with sepals that are pink in the color with a white edge.
4. 'Hort 10-080-01' exhibits sterile flowers that are star-shaped with sepals that are ovate in shape with pointed tips.

The female parent of 'Hort 10-080-01' differs from 'Hort 10-080-01' in being a lace-cap type *hydrangea* and in having single sterile flowers that are paler pink in color. The male parent of 'Hort 10-080-01' differs from 'Hort 10-080-01' in being a lace-cap type *hydrangea*, in having semi-double flowers, and in having sterile flowers that are paler pink n color with white margins. 'Hort 10-080-01' can be most closely compared to the *Hydrangea macrophylla* cultivars 'Hanabi' (not patented) and 'Hort 10-087-01' (copending U.S. Plant patent application Ser. No. 15/330,657). Both cultivars are similar to 'Hort 10-080-01' in having star-shaped, double flowers. 'Hanabi' differs from 'Hort 10-080-01' in being a lace-cap type *hydrangea*, in having flowers that are white in color, and in having much longer peduncles. 'Hort 10-087-01' differs from 'Hort 10-080-01' in having flowers that are pink in color (with white margins), in having slightly stronger stems, in having fewer fertile flowers per inflorescence, and in having a more compact plant habit.

BRIEF DESCRIPTION OF THE DRAWINGS

The accompanying colored photographs illustrate the overall appearance and distinct characteristics of the new *Hydrangea*. The photographs were taken of a plant two years in age as grown in a 4-liter container outside under a shade screen in Boskoop, The Netherlands.

The photograph in FIG. 1 provides a side view of the plant habit of 'Hort 10-080-01' in bloom.

Figure 1:
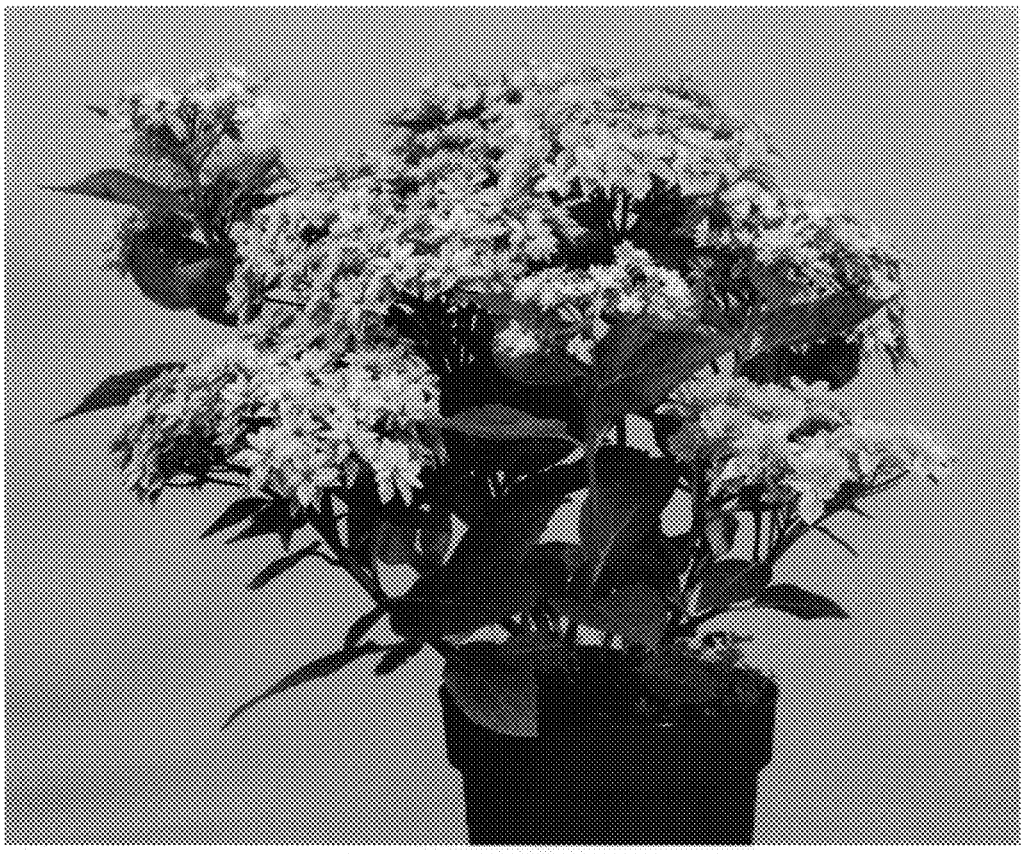
Figure 2:
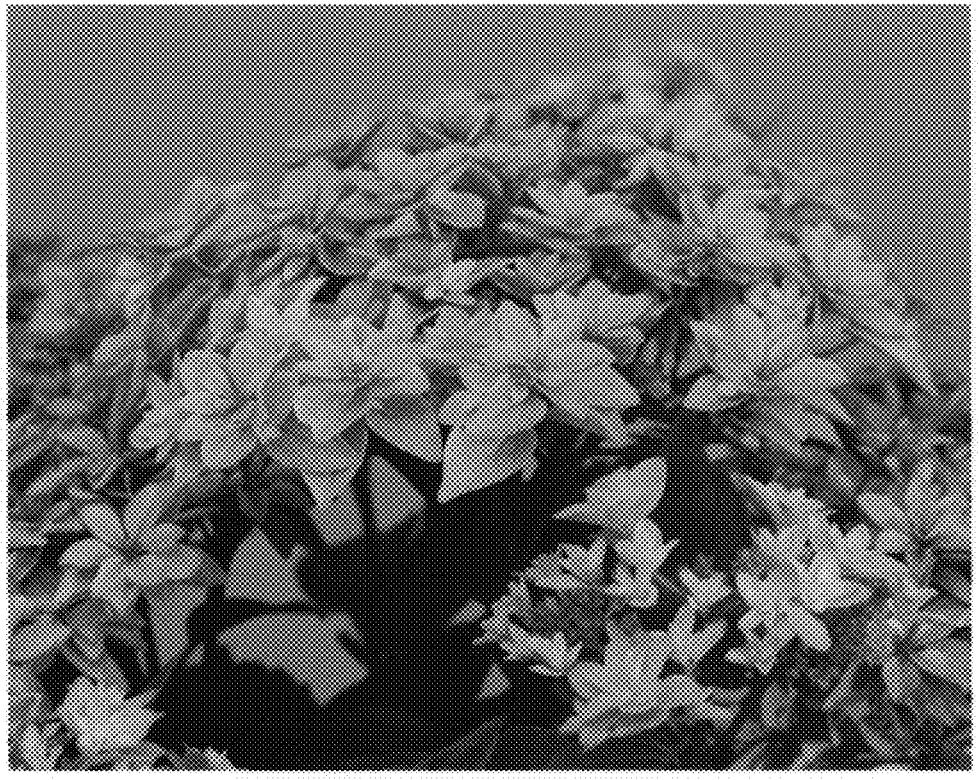

The photograph in FIG. 2 provides a close-up view of an inflorescence of 'Hort 10-080-01'.

Figure 3:
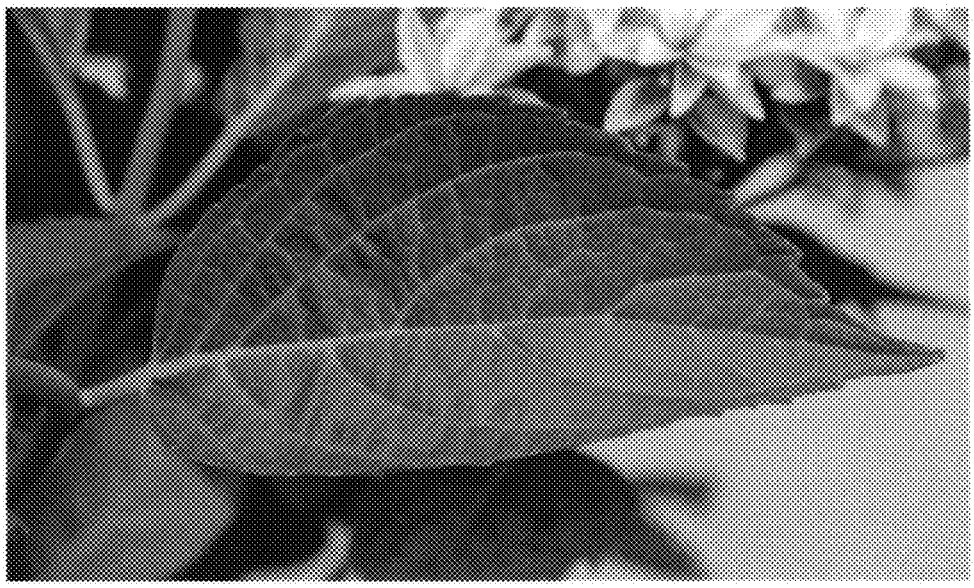

The photograph in FIG. 3 provides a close-up view of a leaf of 'Hort 10-080-01'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown in 4-liter containers outside under a shade screen in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—From May to July in a greenhouse and from July to September outside in The Netherlands.

*Plant type*.—Perennial shrub, mophead-type *hydrangea*.

*Plant habit*.—Upright and compact.

*Height and spread*.—Up to 1 m in height and 1.5 m in spread in the landscape.

*Hardiness*.—At least in U.S.D.A. Zones 5 to 9.

*Diseases and pests*.—No susceptibility and resistance to pests and diseases has been observed.

*Root description*.—Fibrous and fine, 199D in color.

*Propagation*.—Stem cuttings.

*Time required for root development*.—An average of 3.5 weeks for root initiation with a young rooted plant produced in an average of six months.

*Growth rate*.—Moderate.

Stem description:

*Stem shape*.—Rounded.

*Stem strength*.—Strong.

*Stem aspect*.—Upright to an average angle of 30° to soil.

*Stem color*.—Immature and mature stems; 144A lightly suffused with a blend between N186A and 200A at the internodes, older bark; 199A to 199C.

*Stem size*.—An average of 23.3 cm (excluding the inflorescence) in length and 6 mm in diameter.

*Stem surface*.—Immature and mature stems; glabrous, glossy.

*Branching*.—Moderately branched with an average of 11 lateral branches, branching improves with pinching.

*Internode length*.—An average of 6 cm.

Foliage description:

*Leaf shape*.—Ovate to broadly ovate.

*Leaf arrangement*.—Opposite.

*Leaf division*.—Simple.

*Leaf number*.—An average of 8 (4 pairs) per lateral branch.

*Leaf base*.—Rounded to cuneate.

*Leaf apex*.—Acuminate to acute.

*Leaf margins*.—Lower ⅓ of leaf blade; entire, upper ⅔ of leaf blade; serrate to dentate.

*Leaf venation*.—Pinnate, color; upper surface 144C and lower surface; 145B.

*Leaf size*.—An average of 11.1 cm in length and 7.3 cm in width.

*Leaf attachment*.—Petiolate.

*Leaf surface*.—Upper surface; glabrous, very slightly glossy, and moderately rugose, lower surface; glabrous, dull, and moderately rugose.

*Leaf color*.—Young leaves; upper surface 144A and lower surface 144B, mature leaves; upper surface 137B with narrow margins towards the apex 175B to 175C and lower surface 147B to 147C.

*Petioles*.—Flattened, an average of 2.1 cm in length and 3.25 mm in width, color; upper surface 144B lightly suffused with a blend between N186A and 200A towards the stem and lower surface 144A to 144B lightly suffused with N186A and 200A towards the stem, upper surface; glabrous, smooth and very slightly glossy, lower surface; glabrous, smooth, and moderately glossy.

Inflorescence description:

*Inflorescence type*.—Flattened globular, mophead, compound corymb of rotate-shaped double sterile flowers.

*Lastingness of inflorescence*.—Sterile flowers; an average of 6 weeks, persistent, fertile flowers; an average of 3 weeks, persistent.

*Inflorescence number*.—One per lateral stem.

*Inflorescence size*.—An average of 13.4 cm in height and 22.2 cm in diameter.

*Flower number*.—An average of 86 sterile flowers and 130 fertile flowers per inflorescence.

*Flower fragrance*.—None.

*Flower aspect*.—Sterile flowers; upright to slightly outwards, fertile flowers; upright.

*Flower size*.—Sterile flowers; an average of 4.8 cm in diameter and 2.6 cm in depth, fertile flowers; an average of 1 cm in diameter and 7 mm in depth.

*Flower shape*.—Sterile; rotate and double, fertile flowers; rotate with sepals and a deformed gynoecia.

*Flower buds*.—Sterile flowers; an average of 8 mm in length and 6 mm in diameter, ovate in shape, color; 150D suffused with 61D towards the apex, fertile flowers; an average of 3 mm in length and 2 mm in diameter, obovate in shape, color; 144C.

*Peduncles*.—An average of 7 cm in length and 3.3 mm in diameter, held upright, color; 143C heavily suffused with 61B, very slightly glossy surface is sparsely covered with short adpressed hairs; an average of 0.5 mm in length and NN155D in color, smooth, glabrous surface.

*Pedicels*.—Sterile flowers; an average of 4.5 cm in length and 1.5 mm in diameter, held at an average angle of 27.5° to peduncle, 63B in color, strong, very slightly glossy surface is sparsely covered with short adpressed hairs; an average of 0.5 mm in length and NN155D in color, smooth, glabrous surface, fertile flowers; an average of 9 mm in length and 0.75 mm in diameter, held at an average angle of 25° to peduncle, 64B in color, moderate strength, slightly glossy, smooth, and glabrous surface.

*Petals*.—Sterile and fertile flowers; not present.

*Sepals*.—Sterile flowers; an average of 19, arrangement; rotate and double in four whorls, ovate to elliptic in shape, cuneate base, acute to acute-rounded apex, entire margin, an average of 2.1 cm in length and 1.3 cm in width, color; upper surface when opening 62A heavily suffused with 61D at the apex, lower surface when opening 62B, upper surface when fully open 62A with margin areas of 155A, lower surface when fully open 63C to 63D, color fades to 145A on both surfaces, upper surface; glabrous, dull, and slightly velvety, lower surface; glabrous and dull, fertile flowers; an average of 8, rotate in arrangement, elliptic to narrow obovate in shape, narrowly acute apex, cuneate base, entire margin, an average of 5 mm in length and 2 mm in width, color; upper surface when opening N66D, lower surface when opening 68C to 68D, upper and lower surface when fully open 70D, color does not fade, both surfaces smooth and glabrous.

Reproductive organs:

*Gynoecium*.—Sterile flowers; an average of 3 pistils, an average of 1 mm in length, stigma; club-shaped and 70A in color, style; 0.5 mm in length and 70A in color, ovary is 70A in color, fertile flowers; an average of 4, an average of 2 mm in length, stigma; club-shaped and 157A in color, style; 1 mm in length and 144B in color, ovary is 144B in color.

*Androecium*.—Sterile and fertile flowers; not present.

*Fruit and seed*.—No seeds or fruit observed.

It is claimed:

1. A new and distinct cultivar of *Hydrangea* plant named 'Hort 10-080-01' substantially as herein illustrated and described.

* * * * *